United States Patent [19]

Haines

[11] Patent Number: 4,852,586

[45] Date of Patent: Aug. 1, 1989

[54] SENSORY TRANSMITTING MEMBRANE DEVICE

[76] Inventor: Bernard M. Haines, 31 Chaparral Cir., Glenwood Springs, Colo. 81601

[21] Appl. No.: 161,087

[22] Filed: Feb. 26, 1988

[51] Int. Cl.⁴ .............................................. A61F 13/00
[52] U.S. Cl. ..................................... 128/842; 128/844
[58] Field of Search ............ 128/127, 128, 130, 132 R, 128/157, 844, 842, 843; 604/347, 348, 349; 2/21

[56] References Cited

U.S. PATENT DOCUMENTS

| | | | |
|---|---|---|---|
| D. 246,119 | 10/1977 | Okamoto | 604/349 |
| 2,285,981 | 6/1942 | Johns | 604/349 |
| 2,379,624 | 7/1945 | Chisnell | 2/21 |
| 2,586,674 | 0/0000 | Lonne | 128/844 |
| 2,670,736 | 3/1954 | Dunkelberger | 2/21 |
| 2,966,691 | 1/1961 | Cameron | 2/21 |
| 3,659,599 | 5/1972 | McLaughlin | 128/132 R |
| 3,809,090 | 5/1974 | Poulacs et al. | 604/347 |

FOREIGN PATENT DOCUMENTS 0938465 10/1963 United Kingdom ................ 604/309

Primary Examiner—Robert A. Hafer
Assistant Examiner—Michael Brown
Attorney, Agent, or Firm—William D. Stokes

[57] ABSTRACT

A device for the transmission and enhancement of tactile sensations transmitted across a barrier membrane, particularly condoms, finger cots and gloves used to prevent transmission of disease organisms between contacting body tissues. The device has a plurality of antipodal pairs of projections extending through the barrier membrane whereby the barrier membrane acts as a fulcrum for the transmission of movement by one projection of an antipodal pair to the other member of the projection pair.

12 Claims, 1 Drawing Sheet

SENSORY TRANSMITTING MEMBRANE DEVICE

BRIEF DESCRIPTION OF THE INVENTION

The present invention is directed to a device useful in the transmission of tactile sensations. In particular, the invention concerns a protective type material wherein acute tactile sensations are transmitted from one side of the material to the other. More particularly the invention is directed to a novel construction for prophylactic devices such as surgical gloves and condoms.

BACKGROUND OF THE INVENTION

The usefulness, indeed, urgent need for the use of condoms, particularly in casual sexual activities is well established and documented. Notwithstanding cogent pathological reasons for the use of condoms, sexual partners in general, have been reluctant to use such devices. Most often the refusal to use condoms is based on the loss of tactile sensation by one or both partners during copulation when the penis is sheathed with the type condoms presently available. Of no less importance than the desirability of preventing the loss of tactile sensation by the use of condoms in sexual intercourse is the prevention of loss of tactile sensations when using gloves in procedures requiring aseptic conditions, for example, surgery, particularly where visual perception of the field of procedure is limited.

It may well be appreciated the desirability of having a device which, in addition to being impervious to the passage of either pathogens or sperm, will not cause the loss of tactile sensations, and generally enhance the sensory perception of the user. The principal thrust of the art has long been the discovery of a prophylactic device by which the sensory perception of the user will minimally achieve the normal tactile sensation of an unsheathed organ. Unfortunately, none of the devices known in the art have been successful.

Numerous constructions have been proposed for devices to improve the transmission of sensory sensation in a prophylacterically sheathed organ as shown for example in U.S. Pat. No. 3,809,090 to Povlacs et al. wherein is disclosed a condom having rigid projections on the outer surface. Such devices are intended to provide mechanical stimulation by one side of the prophylactic device rather than enabling transmission of sensory perceptions. Moreover, such rigid devices suffer the disadvantage of often causing severe irritation to delicate tissues.

In accordance with the invention, there is provided a device which enables the two-way transmission of tactile sensation and perception through the pellicle of prophylactic devices such as condoms, finger cots, and gloves used in sterile operations which, not only enables the tactile sensation of an unsheathed organ, but also amplifies the transmission of the tactile sensation through the prophylactic device.

SUMMARY OF THE INVENTION

The present invention provides a device for enabling and enhancing the transmission of tactile sensations across a prophylactic membrane barrier. In accordance with the invention, there is provided a plurality of pairs of shaped projections spaced apart and arranged to form, juxtaposed or apposing pairs, integrally formed with, and coaxially extending from, the opposite sides of a base, prophylactically impermeable, flexible sheet material or pellicle. In a preferred embodiment, the projection pairs are generally cylindrical in shape. It will be appreciated that in the preferred embodiment, and particularly for manufacture of the condoms and gloves of the invention, the prophylactically impermeable sheet material is of thin, latex rubber or other inert elastomeric material. In the device of the invention, wherever any force acts on one of the projections of a projection-pair, the flexible base material or pellicle allows motion of its antipodal projection by serving as a fulcrum for pivoting and moving the projection. In addition, whenever any force having a component perpendicular to the base material acts on one member of a projection-pair, the flexible material will allow perpendicular motion of the apposing projection by stretching of the pellicle. Other motions such as vibratory and rotational are transmitted between the antipodal projection-pairs in a similar manner.

It will be perceived hereinafter from the description and drawings of the device that any force acting on and causing motion of one member of an antipodal projection-pair of either side f the flexible material will result in, if unobstructed, a corollary or opposite motion of its apposite or antipodal projection member. In the device of the invention, complex motions, for example, vibratory and rotatory, are also transmitted between projection-pairs. The sized and dimensions of the antipodal pairs of projections is determined by intended use of the material. The invention not only minimally allows transmission of tactile sensations across the barrier material, substantially as in the contacting of two surfaces without the interposition of a barrier material, but also amplifies the transmission of tactile sensations through the plurality of unitary, separate and distinct contact points individually responding to the most subtle movement or anomaly.

Condoms of the inventive device provide transmission of the most delicate of movement by contacting organs, for example, either penis or vagina during intercourse. Where the device is a surgical glove, the transmission of tactile sensory perception of anatomical anomalies is enabled during operational procedures, particularly when the field of sight is limited as during surgery. It will be appreciated that the actual motion, intensity, and sensitivity transmitted between antipodal pairs of the invention depend upon many variables, for example, magnitude, direction and duration of force, size of anomaly, pellicle material, thickness of pellicle, pattern, spacing, size and shape of the projections. Embodiments of the invention provide different shapes for the projection pair members including concave-ended cylindrical, conical, flat-ended cylindrical, and beveled spherical and combinations thereof which different shapes may be used to enhance the tactile transmissions of particular movements or anomalies as the case may be.

BRIEF DESCRIPTION OF DRAWINGS

FIG. 5 illustrates different shapes of projections which may be used in embodiments of the invention.

DETAILED DESCRIPTION OF THE DRAWINGS

Figure 1:
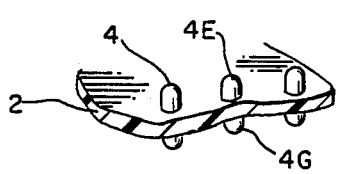
FIG. 1 is a representational fragmentary, perspective view of the device of the invention illustrating the rounded-end, cylindrically-shaped coaxial pairs of projections extending on both sides of the pellicle.

Referring to the drawings, particularly FIGS. 1, 2, 3, 4, 5, 6, 7 and 8, in which like parts or elements have the same number, there is shown a device having a flexible base material, pellicle, or barrier membrane 2 through which extends a plurality of coaxial pairs of projections 4 integrally molded therewith. The device is preferably formed of a single, homogenous prophylactically impervious, elastomeric material.

Figure 2:
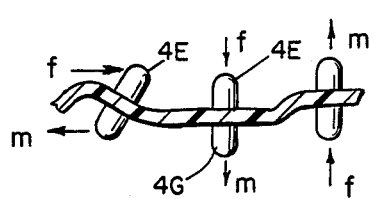
FIG. 2 is a view of the device of FIG. 1 in operation illustrating movement of the projections responsive to forces applied to a single projection of an apposing pair of projections.

Referring particularly to FIG. 1, the projections 4 consist of pairs of projections 4E and 4G. The projections illustrated in FIG. 1 are in the undisturbed or rest position. FIG. 2 illustrates the responsive movement and direction of movement of antipodal pair members 4E and 4G of FIG. 1 when a force f is applied from different directions to one projection of an apposed pair. In the illustration of FIG. 2, the force f, direction of the force indicated by arrows, is shown applied horizontally to one projection, vertically downward to another projection and vertically upward to another. The direction of the responsive movement m of a projection to the force f applied to its apposing member is indicated by arrows.

Figure 3:
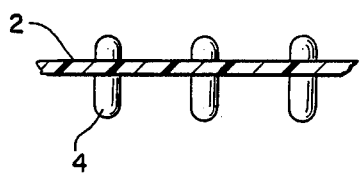
FIG. 3 is a representational fragmentary, cross-sectional view of an embodiment of the invention where the projections of each pair of coaxial projections are of unequal length.
Figure 4:
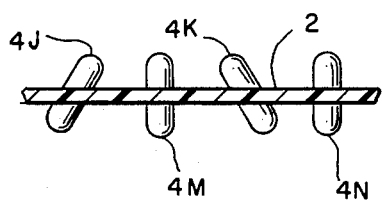
FIG. 4 is a representational fragmentary, cross-sectional view of an embodiment of the invention wherein various coaxial pairs of projections are constructed at different angles with respect to the pellicle and each other.

In FIG. 3, there is shown an embodiment of the invention wherein the length of one projection of each pair 4 differs from its apposing member. Still another embodiment of the invention is illustrated in FIG. 4 wherein antipodal pairs 4J and 4K are shown constructed at opposing angles to each other and at an angular orientation with respect to vertically disposed pairs 4M and 4N.

It will be appreciated that in a condom of the invention, each apposing projection pair may be constructed at varying angles with respect to adjacent projection pairs to bring about the simultaneous transmission of multiple and varying tactile sensations across the barrier membrane in both directions responsive to varying movements and contours of tissues contacting either side of the device. This construction and the construction illustrated in FIG. 3 is very useful in, for example, the surgical glove embodiment of the invention whereby a magnification, or concentrated, tactile response is transmitted to the fingertips by physical anomalies such as tumors.

Figure 5:
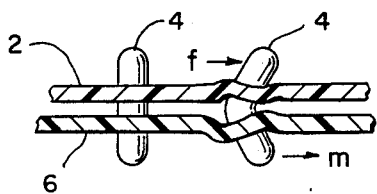
FIG. 5 is a cross-sectional view of an embodiment of the device of the invention comprising a doubled wall base membrane material.

Referring specifically to FIG. 5, there is illustrated an embodiment of the invention in which the flexible base material is double-walled comprising separate and parallel barrier membranes 2 and 6. Projection pairs 4 extend through both membrane members. Membrane members 2 and 6 move generally independent of each other. The effect of such construction is that each antipodal pair member will move in the same direction as the direction of the force applied to its apposing projections member as shown by arrows, designated respectively as f and m, indicating force and direction applied to a projection and the direction of movement of its apposing member. A lubricant material may be sealed within the space formed by the parallel membranes to facilitate movement between the pair of pellicles and prevent drag therebetween.

Figure 6:
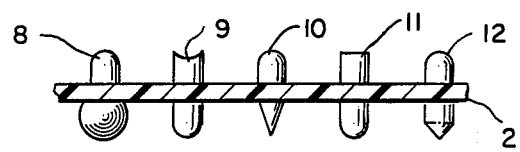

As mentioned hereinbefore, the projection members of the device may be shapes other than cylindrically-shaped having convex ends. As illustrated in FIG. 6, other projection shapes are shown as numerals 8, 9, 10, 11 and 12. It will be observed that the apposing projection members of each antipodal pair is shown to have a different shape, and it will be understood that such differences in shape will not affect the responsive movement of a projection member to a force applied to the apposing projection. Difference in shape may be used to magnify, augment, or change sensory transmission in accordance with the various uses for which the device of the invention is used.

Figures 7, 9:
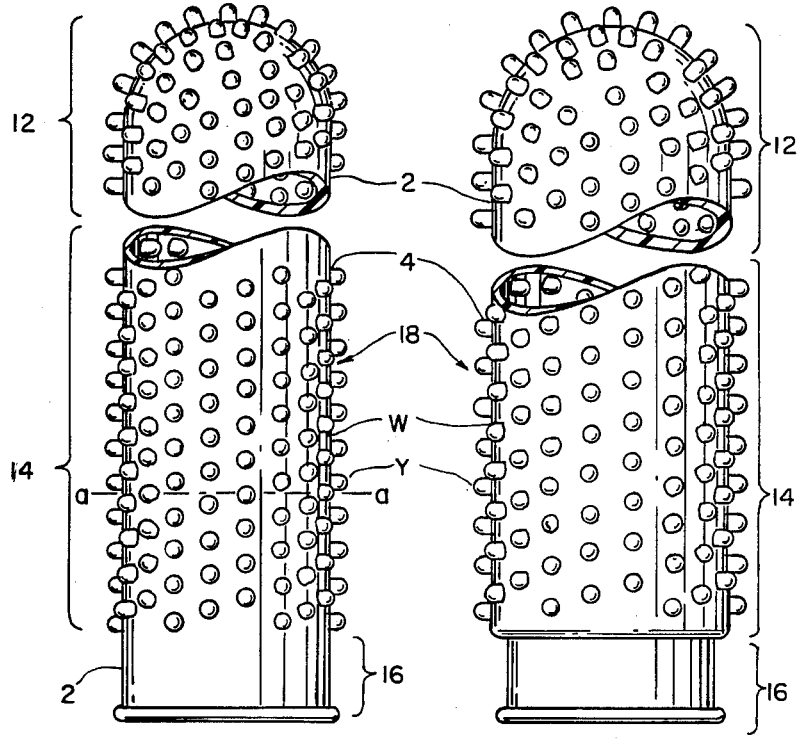
FIG. 7 is a fragmentary view of a condom of the invention.
FIG. 9 is a fragmentary view of another condom embodiment of the invention.
Figure 8:
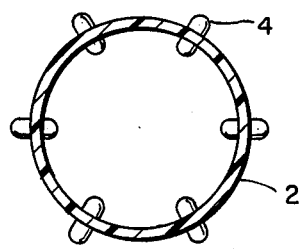
FIG. 8 is a cross-section taken on lines 1—1 of the condom of FIG. 7.

In FIGS. 7 and 8, there is shown an embodiment of a condom 10 of the invention having an impermeable, elastomeric pellicle 2, a closed head portion 12 and a cylindrical body portion 14, terminating in an open end portion 16. A plurality of continuous coaxial pairs of projections 4 extend through the body portion 14 and head portion 12. The condom is formed of a unitary material in which the projections are integrally formed. The projection pairs 4 are intermittently spaced in the body 14 and head portion 12. It will be understood that the number and spacing of the coaxial pairs is a matter of choice; however, in the embodiment illustrated the projections are disposed in spiral rows and in vertical alignment over substantially the entire body portion 14 and head portion 12 of the condom. The open-ended portion 16 is free of projections to insure a tight fit of the condom about the base of the penis, or the base of the fingers in a finger cot to prevent leakage of seminal discharges, or transmission of disease organisms. In a preferred embodiment of a condom as illustrated by FIG. 9, the cylindrically-shaped head portion 12 and body portion 14, are larger in diameter than the open-end portion 16 which, as previously mentioned is designed to tightly enclose the base of the penis. The larger diameter of the body and head portions allow the condom to act much as a foreskin in an uncircumcised penis allowing the pellicle 2 to slide up and down along the surface of a penis with consequent provision of a more flexible and mobile fulcrum for enhancing the movement of the antipodal projections. An increased diameter of the order of 2 mm to 4 mm provides excellent results. It will be appreciated that the glove embodiments of the invention may be similarly constructed.

As pointed out hereinbefore, the device of the invention is formed of a unitary prophylactically, impermeable elastomeric material, for example, latex or rubber, which is highly flexible and elastic. The elastomeric material is preferably of a uniform thickness throughout the projections, solid as opposed to hollow. The integral construction of the device of the invention including the pellicle and projections thereon, may be manufactured using any of the well known molding processes of the art. By way of example, the device may be formed by an injection molding technique using a die comprising a one-piece internal mandrell and a plurality of external segments. The external segments may be manually removed and stripping or air injection used to remove the molded device from the internal mandrell. As measured from the internal and external surfaces of the pellicle, the minimum internal and/or external projection heights of the projection pairs is about 0.15 mm, but the preferred height is approximately 1.5 mm. The minimum effective diameter of the projections is 0.1 mm while the preferred diameter is about 1.0 mm. The preferred spacing between the projections is about 3 mm and the maximum spacing about 5 mm. For maximum stimulation the projections cover substantially the entire surfaces of the head portion 12 and body portion 14 of a condom.

It will be obvious to those skilled in the art from reading the description of the invention that numerous modifications and changes may be made without departing from the spirit and scope of the invention.

What is claimed is:

1. A device for the transmission of tactile and anomalous sensations between surfaces, at least one of which is living tissue, comprising a substantially homogenous, elastomeric material base having a plurality of projection pairs spaced apart and integrally formed with said base material, each projection pair comprising two continuous coaxial projections extending from the opposite sides of said material base.

2. The device of claim 1 wherein said homogenous, elastomeric base is prophylactically impervious.

3. A prophylactic device is accordance with claim 1 having a substantially cylindrical body portion, a closed-end head portion, and an open-end bottom portion.

4. A prophylactic device in accordance with claim 3 in which said cylindrical body portion and said head portion are larger in diameter than said bottom portion.

5. The device of claim 1 wherein each projection of an antipodal pair is a different height from the base.

6. The device of claim 3 wherein said plurality of projection pairs are disposed in said head and body portion of the device.

7. The device of claim 1 wherein said base is a two-wall elastomeric membrane, and each projection of a projection pair are integrally connected and continuously coaxial to each other through both of said walls.

8. The device of claim 1 wherein the projections are generally cylindrically-shaped.

9. The device of claim 1 wherein the projections extend from the surfaces of the base at different angles with respect to the perpendicular.

10. A prophylactic device comprising a body of substantially homogenous, elastomeric material having a substantially cylindrical body portion, a closed-end head portion and an open-end bottom portion, said body and head portions being formed with a plurality of spaced apart exteriorly and interiorly extending continuous coaxial pairs of projections extending from opposite side of said base material.

11. The prophylactic device of claim 10 in which said cylindrical body portion and said closed-end head portion are larger in diameter than said bottom portion.

12. The prophylactic device of claim 10 wherein said projections are spirally spaced in vertical alignment.

* * * * *